United States Patent
Stefan

(10) Patent No.: US 9,599,166 B2
(45) Date of Patent: Mar. 21, 2017

(54) COUPLING BETWEEN TWO PARTS OF A MEDICAL INSTRUMENT

(71) Applicant: Karl Storz GmbH & Co. KG, Tuttlingen (DE)

(72) Inventor: Jochen Stefan, Wald (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 855 days.

(21) Appl. No.: 13/864,915

(22) Filed: Apr. 17, 2013

(65) Prior Publication Data

US 2013/0310812 A1 Nov. 21, 2013

(30) Foreign Application Priority Data

Apr. 18, 2012 (DE) .................. 10 2012 007 651

(51) Int. Cl.
*F16D 1/08* (2006.01)
*A61B 17/29* (2006.01)
*A61B 17/00* (2006.01)

(52) U.S. Cl.
CPC ............ *F16D 1/0876* (2013.01); *A61B 17/29* (2013.01); *A61B 34/70* (2016.02); *A61B 2017/00473* (2013.01); *A61B 2017/00477* (2013.01); *A61B 2017/2931* (2013.01); *Y10T 29/49826* (2015.01); *Y10T 29/49995* (2015.01); *Y10T 403/7007* (2015.01)

(58) Field of Classification Search
CPC ......... A61B 18/18; A61B 17/29; A61B 19/22; A61B 2017/00473; A61B 2017/00477; A61B 2017/2931; A61B 17/608; A61B 17/04; F16D 1/0876; Y10T 29/49995; Y10T 29/49826

USPC ..... 623/1.11; 604/506; 600/104, 154; 606/1, 606/205

See application file for complete search history.

(56) References Cited

U.S. PATENT DOCUMENTS

| | | | |
|---|---|---|---|
| 5,782,748 A * | 7/1998 | Palmer ................... | A61B 10/06 600/104 |
| 5,792,165 A * | 8/1998 | Klieman ................. | A61B 17/29 606/170 |
| 2003/0120272 A1* | 6/2003 | Schneider ........ | A61B 17/00234 606/49 |
| 2006/0149131 A1* | 7/2006 | Or ....................... | A61B 1/00142 600/154 |
| 2006/0276772 A1* | 12/2006 | Moos .................... | A61B 10/025 604/506 |
| 2006/0282117 A1* | 12/2006 | Berberich .......... | A61B 17/0483 606/205 |
| 2008/0021278 A1* | 1/2008 | Leonard ............. | A61B 17/1608 600/129 |
| 2011/0046610 A1 | 2/2011 | Schaeffer | |
| 2011/0306952 A1 | 12/2011 | Chen | |

(Continued)

FOREIGN PATENT DOCUMENTS

DE 4133350 A 8/1992

*Primary Examiner* — William Thomson
*Assistant Examiner* — Victor Shapiro
(74) *Attorney, Agent, or Firm* — Whitmyer IP Group LLC

(57) ABSTRACT

A tool for a medical instrument includes a coupling member on the proximal end of the tool, for releasable mechanical coupling with a distal end of a shaft of a medical instrument, wherein the coupling member is in the form of a helical cutout of a circular cylinder barrel.

14 Claims, 4 Drawing Sheets

(56) References Cited

U.S. PATENT DOCUMENTS

2011/0307049 A1* 12/2011 Kao .................. A61F 2/966
623/1.11

* cited by examiner

COUPLING BETWEEN TWO PARTS OF A MEDICAL INSTRUMENT

FIELD OF THE INVENTION

The present invention refers to a tool, a handling device and a shaft for a medical instrument, to a medical instrument and to a method for producing a coupling on a proximal end of a tool or on a proximal or distal end of a shaft or on a handling device for a medical instrument.

BACKGROUND OF THE INVENTION

The regulations for cleaning and sterilizing re-usable surgical instruments make greater and greater demands which necessitate an ever more extensive ability to take apart re-usable surgical instruments. At the same time, instruments for micro-invasive interventions, in particular, are becoming smaller and smaller, in particular the cross sections and diameters of the shaft and the tool on the distal end of the shaft. Couplings, which are conventionally provided for releasable mechanical coupling between the tool and the shaft, however, are not able to be miniaturized in an arbitrary manner. Where a shaft diameter is 3.5 mm or less, new concepts for releasable mechanical coupling between the tool and shaft are necessary.

SUMMARY OF THE INVENTION

An object of the present invention is to create an improved tool and an improved shaft for a medical instrument, an improved medical instrument and an improved method for producing a coupling member.

Said object is achieved by the objects of the independent claims.

Further developments are provided in the dependent claims.

Exemplary embodiments of the present invention are based on the idea of creating a releasable, positive locking connection between the tool and the shaft of a medical instrument by means of two helical strips which can be twisted together. The interlocking helical-strip-shaped coupling members on the shaft and the tool together form an (in particular thin-walled) circular cylinder barrel. In other words, the two corresponding coupling members on the tool and the shaft can be imagined as being formed from a tube in the form of a circular cylinder barrel by means of a section along a closed path, the closed path having (at least) two parallel helical portions and between their ends, for example, two portions which extend in the circumferential direction.

A certain similarity with a screw-type connection exists with regard to the relative movements of the two coupling members when producing and releasing a mechanical connection. The coupling members, however, do not form interlocking internal and external threads. In particular, there is no need for either a hollow or a solid core on which radially outwardly protruding webs form the thread flights (external thread). Neither is an outer barrel nor a sleeve on which radially inwardly protruding webs form a thread flight (internal thread) necessary. Rather, the coupling members are, in each case, approximately in the form of a corkscrew with a center web. The coupling members are, therefore, in particular—different to the helical webs on a conventional internal or external thread—self-supporting or at least self-supporting in part.

A simple experiment with two identical corkscrews with a center web shows that the core of a conventional external thread and the tube-shaped, sleeve-shaped or barrel-shaped region about a conventional internal thread, which are missing in the case of a corkscrew with a center web, also have the function of preventing relative displacement and relative tilting of the two threads. The present invention is also based on the idea that said function can be met by an element which is arranged inside or outside the coupling members and is not rigidly connected to either of the two coupling members. Rather, for example, the transmission rod for transmitting a force and/or a torque between a proximal end and a distal end of a medical instrument can be realized such that it essentially abuts on the inside against the coupling members. Although the transmission rod is not rigidly connected to either of the two coupling members, but is displaceable lengthwise in relation to both of them and/or is rotatable about the longitudinal axis, it can prevent relative displacement at right angles to the longitudinal axis and relative tilting of the coupling members which would otherwise be possible as a result of unavoidable elasticity of the coupling members and as a result of unavoidable mechanical play between the coupling members.

Exemplary embodiments of the present invention are based on the idea of creating a releasable, positive locking connection between the tool and the shaft of a medical instrument by means of two interlocking coupling members on the tool and the shaft, the coupling members in each case being in the form of a cutout of a circular cylinder barrel.

A tool for a medical instrument includes a coupling member on the proximal end of the tool, for releasable mechanical coupling with a distal end of a shaft of the medical instrument, wherein the coupling member is in the form of a substantially helical cutout of a circular cylinder barrel.

A tool for a medical instrument includes a coupling member on the proximal end of the tool, for releasable mechanical coupling with a distal end of a shaft of a medical instrument, wherein the coupling member is in the form of a cutout of a circular cylinder barrel, wherein the tool is realized for coupling with a coupling member, which is also in the form of a cutout from a circular cylinder barrel, on the distal end of a shaft.

In particular, the tool and the coupling member are provided and realized for coupling with a coupling member which is in the form of a substantially complementary cutout of the identical circular cylinder barrel.

The medical instrument is, in particular, an instrument for micro-invasive surgical interventions. The medical instrument includes, in particular, a handling device with one or several gripping parts which can be moved in relation to one another in a manual manner, a shaft which, as a rule, is long and thin and the tool which can be connected to the distal end of the shaft by means of the coupling member. The tool is, for example, a pair of forceps, scissors, a punching tool, a needle holder or another tool with one or two movable mouth parts or a hook or another movable or non-movable acting device.

In this respect in particular, the coupling member is in the form of a cutout of a circular cylinder barrel having a predetermined wall thickness when it has an inner and an outer surface which are formed by mutually corresponding cutouts from the circular cylindrical inner lateral surface of the circular cylinder barrel and from the circular cylindrical outer lateral surface of the circular cylinder barrel. Differently to, for example, the carriers in the case of a conventional bayonet coupling, no part of the coupling member projects inward beyond the inner lateral surface of the circular cylinder barrel or outward beyond the outer lateral surface of the circular cylinder barrel.

In the case of a tool, as is described here, the coupling member is in the form, in particular, of a helical-strip-shaped cutout of a circular cylinder barrel or in the form of a cutout of a circular cylinder barrel, the width of which reduces continuously or discontinuously in the proximal direction.

Where it is in the form of a helical-strip-shaped cutout of a circular cylinder barrel, the width of the coupling member, in particular, is constant, it being possible to measure the width in each case in the circumferential direction or in the direction at right angles to the helical edges of the coupling member. A particularly low play, precise coupling with a correspondingly realized coupling member of a shaft can be possible with a strip shape or a constant width.

Where it is in the form of a cutout of a circular cylinder barrel, the width of which reduces continuously in a proximal direction, the width is, in particular, an affine-linear function of the coordinates measured parallel to the longitudinal axis of the tool and the shaft. Said form is also called a helical-wedge-shaped form. With a width which reduces continuously or discontinuously or in a stepped manner in the proximal direction, it is possible to adapt the width to the forces and torques to be transferred or absorbed at every location. The coupling member can be realized so as to be wide at its distal end, where it has to transfer the largest forces and torques, and narrow at its proximal end. In reverse, a corresponding coupling member on the distal end of a shaft can be realized so as to be narrow distally and wide proximally. This can give a high level of rigidity overall to the coupling between the tool and the shaft. In addition, a width which reduces in the proximal direction can simplify a coupling with a coupling member, the width of which reduces in the distal direction.

The coupling member can be realized in a comparatively thin-walled manner, in particular thinner walled than a threaded sleeve with an internal or external thread. As a result, the coupling member can make more extensive miniaturization possible.

In the case of a tool, as is described here, the coupling member is formed, in particular, from a tube.

The tube, from which the coupling member is formed, has, in particular, a circular ring-shaped cross section. The coupling member is formed from the tube in particular by means of laser cutting. As, in this case, no force acts on the tube and it is consequently not deformed, the coupling member can be produced in a particularly precise manner by means of laser cutting.

A tool, as is described here, additionally includes, in particular, a transmission rod for transmitting at least either a force or a torque between a proximal end and a distal end of a shaft which is coupled with the tool, wherein the inside diameter of the circular cylinder barrel corresponds substantially to the outside diameter of the transmission rod.

The inside diameter of the circular cylinder barrel corresponds, in particular, apart from the play necessary for the low-friction mobility of the transmission rod, to the outer diameter of the transmission rod. The transmission rod has, in particular, a circular cross section for this purpose. As an alternative to this, the transmission rod has, for example, a star-shaped or polygonal cross section in the region of the coupling member such that it abuts against the coupling member on the inside along several lines or abuts in a substantial manner and is able to support the same. The tool and the transmission rod can be realized and coupled together in a mechanical manner such that a movement of the transmission rod in relation to the tool in the proximal direction brings about a closing movement on the tool and a movement of the transmission rod in relation to the tool in the distal direction brings about an opening movement on the tool (or vice versa).

As already mentioned, the transmission rod, although it is not rigidly connected to the coupling member but is movable in relation to said coupling member, can support the coupling member from the inside and force a desired positioning and aligning of the coupling member of the tool in relation to a corresponding coupling member on the distal end of a shaft. Said dual function or object of the transmission rod can contribute to the ability to miniaturize the coupling member.

A tool, as is described here, additionally includes, in particular, a support sleeve which abuts against the coupling member and is joined to the coupling member.

The support sleeve can abut against the coupling member on the inside or on the outside and can be connected to said coupling member in particular by means of laser welding or soldering. The coupling member—as already mentioned—can be realized to a considerable extent not only for absorption, but (differently to a helical web on a conventional thread) also for diverting or transmitting forces over a wide area. Consequently, the support sleeve can be realized in a particularly thin-walled manner, in particular more thin-walled than a sleeve on which a conventional thread is generated by means of thread cutting. Over and above this, the producing of the coupling member and the joining of the thin-walled support sleeve onto the coupling member can be executable using less material, spending less time and creating less scrap than the production of a conventional thread by means of thread cutting.

In the case of a tool, as is described here, the width of the helical-strip-shaped cutout of the circular cylinder barrel, in particular in the circumferential direction, corresponds to half the circumference of the circular cylinder barrel.

The circumferential direction refers to the circular cylinder barrel or to the circumference thereof (in a plane at right angles to the axis of symmetry of the circular cylinder barrel). A coupling member with the named width corresponds to and is couplable with a coupling member of the same width. In this case, a width which corresponds to half the circumference of the circular cylinder barrel also refers to a width which is slightly smaller than half the circumference in order to make it possible, by means of a small amount of play, for the coupling members to be able to be coupled with low friction. When both coupling members of the tool and of the shaft essentially have the same width, this makes it possible, at a given wall thickness of the coupling members, for the coupling between the tool and the shaft to have maximum rigidity.

As an alternative to this, the helical-strip-shaped cutout of the circular cylinder barrel in the circumferential direction has a width which is smaller than half the circumference of the circular cylinder barrel, in particular a width within the range of a quarter to a third of the circumference of the circular cylinder barrel. This applies in particular when a support sleeve is provided. The stiffening effect of the support sleeve on the coupling member on the tool can, therefore, be utilized in order to realize the coupling member on the tool in a narrower manner and the corresponding coupling member on the shaft in a wider manner and thus to increase the overall rigidity of the coupling member on the shaft.

A tool, as is described here, additionally includes, in particular, a locking bar which is displaceable axially in relation to the coupling member.

Axial displaceability of the coupling member refers to displaceability parallel to the longitudinal axis and/or the axis of symmetry of the shaft, the transmission rod and the circular cylinder barrel. The locking bar is realized, in particular, for the purpose of engaging in a corresponding recess on the coupling member of a shaft to be coupled with the tool in order to lock the mechanical coupling between the tool and the shaft.

A shaft for a medical instrument includes a coupling member on the distal end of the shaft for releasable mechanical coupling with a proximal end of a tool for forming a medical instrument, the coupling member being in the form of a substantially helical cutout of a circular cylinder barrel.

A shaft for a medical instrument includes a coupling member on the distal end of the shaft, for releasable mechanical coupling with a proximal end of a tool, the coupling member being in the form of a helical cutout of a circular cylinder barrel.

The tool is realized on the proximal end of a tool, in particular, for coupling with a coupling member which is also in the form of a cutout from a circular cylinder barrel.

In particular, the shaft and the coupling member are provided and realized for coupling with a coupling member which is in the form of a substantially complementary cutout of the identical circular cylinder barrel.

In the case of a shaft, as is described here, the coupling member is formed, in particular, from a tube.

In the case of a shaft, as is described here, the coupling member is, in particular, in the form of a helical-strip-shaped cutout of a circular cylinder barrel or in the form of a cutout of a circular cylinder barrel, the width of which reduces continuously or discontinuously in the distal direction.

In the case of a shaft, as is described here, in particular the inside diameter of the circular cylinder barrel corresponds substantially to the outside diameter of a transmission rod, for which the shaft is realized.

A shaft, as is described here, additionally includes, in particular, a support sleeve which abuts against the coupling member and is joined to the coupling member.

The support sleeve abuts in particular against the coupling member on the outside.

In the case of a shaft, as is described here, the width of the helical-strip-shaped cutout of the circular cylinder barrel in the circumferential direction corresponds to half the circumference of the circular cylinder barrel.

As an alternative to this, in the case of shaft, as is described here, the width of the helical-strip-shaped cutout of the circular cylinder barrel in the circumferential direction is smaller than half the circumference of the circular cylinder barrel. This applies, in particular, when the above-described support sleeve is provided.

A coupling for a part of a medical instrument which can be taken apart in a non-destructive manner or on a part of a medical instrument which can be taken apart in a non-destructive manner includes a coupling member for releasable mechanical coupling with a corresponding coupling member on another part of the medical instrument, wherein the coupling member is in the form of a substantially helical cutout of a circular cylinder barrel.

A medical instrument which can be taken apart in a non-destructive manner is a medical instrument which—in particular without using a screw driver, a spanner or any other tool—can be repeatedly taken apart into two or more parts and then completely fitted together again so as to be functional. The ability to be taken apart enables or facilitates, in particular, the cleaning and sterilizing of the medical instrument and/or the exchanging of one part of the medical instrument.

The coupling is provided and arranged, in particular, on a distal end of a shaft or on a proximal end of a shaft or on a distal end of a handling device. As an alternative to this, the coupling is provided, for example, for a distal end of a shaft or for a proximal end of a shaft or for a distal end of a handling device.

In particular, the coupling member is provided and realized for coupling with a corresponding coupling member which is in the form of a substantially complementary cutout of the identical circular cylinder barrel.

In the case of a coupling, as is described here, the coupling member is formed, in particular, from a tube.

In the case of a coupling, as is described here, the coupling member is, in particular, in the form of a helical-strip-shaped cutout of a circular cylinder barrel or in the form of a cutout of a circular cylinder barrel, the width of which reduces continuously or discontinuously in the distal direction.

In the case of a coupling, as is described here, the inside diameter of the circular cylinder barrel, in particular, corresponds substantially to the outside diameter of a transmission rod of a medical instrument, for which the coupling is realized.

A coupling, as is described here, additionally includes, in particular, a support sleeve which abuts against the coupling member and is joined to the coupling member.

The support sleeve abuts against the coupling member, in particular on the outside.

In the case of a coupling, as is described here, the width of the helical-strip-shaped cutout of the circular cylinder barrel in the circumferential direction corresponds to half of the circumference of the circular cylinder barrel.

As an alternative to this, in the case of a coupling, as is described here, the width of the helical-strip-shaped cutout of the circular cylinder barrel in the circumferential direction is smaller than half of the circumference of the circular cylinder barrel. This applies, in particular, when the above-described support sleeve is provided.

A handling device or a shaft for a medical instrument which can be taken apart in a non-destructive manner includes a coupling, as is described here.

In the case of a handling device with the coupling, the coupling is arranged, in particular, on the distal end of the handling device. In the case of a shaft with the coupling, the coupling is arranged, in particular, on the distal end or on the proximal end of the shaft.

In the case of a coupling, as is described here, the edges of the helical-strip-shaped cutout enclose, in particular, an angle within the range of between 40° and 70° with the axis of symmetry of the circular cylinder barrel.

In particular, the angle is within the range of between 50° and 65°. In the case of a predetermined number of turns, the angle influences the length of the coupling member. The smaller the pitch or the larger the angle, the shorter the coupling member. At the same time, the angle influences the width of the helical-strip-shaped cutout, measured in a direction at right angles to the helical edges thereof. Said width, measured at right angles to the helical edges of the coupling member, influences the rigidity of the coupling member. The greater the pitch or the smaller the angle, the greater the width of the coupling member in the direction at right angles to its helical edges and its rigidity compared to its length. An angle within the range of between 40° and 70° and even more an angle within the range of between 50° and 65° offers a particularly good compromise and consequently overall particularly good rigidity of the coupling member.

Further possible embodiments, variants, characteristics, features, actions and advantages of a coupling correspond to those described above for a tool.

A medical instrument includes a tool, as is described here, and a shaft, as is described here.

A medical instrument includes a shaft, a tool, a first coupling member on the distal end of the shaft and a second coupling member on the proximal end of the tool, for releasable mechanical coupling with the first coupling member, wherein the first coupling member is in the form of a cutout from a first circular cylinder barrel and the second coupling member is the form of a cutout from a second circular cylinder barrel, wherein the first circular cylinder barrel and the second circular cylinder barrel have the same diameter.

In the case of a medical instrument, as is described here, the coupling members on the shaft and the tool, in particular, are the same.

A sameness of the coupling members refers, in particular, to the mutually corresponding characteristics of the coupling members and does not exclude the components which form the coupling members differing, for example, in the manner of the mechanical coupling with the shaft or with the tool.

A medical instrument, as is described here, additionally includes, in particular, a handling device on the proximal end for handling the medical instrument, the handling device being connected to or releasably connectable to the proximal end of the shaft.

In the case of a method for producing a coupling for or on a proximal end of a tool for a medical instrument or for or on a distal end of a shaft for a medical instrument, a tube is prepared and a substantially helical region of the tube is removed in order to form the coupling member.

Prior to the removal, the tube has, in particular, a circular ring-shaped cross section. The substantially helical region of the tube is removed in particular by means of laser cutting, no forces acting on the tube and said tube not being elastically or plastically deformed, as a result of which a high level of precision is achievable. When the coupling member is provided as a coupling member on a proximal end of a tool, once the substantially helical region has been removed, it can be joined, in particular welded, soldered or bonded, onto the proximal end of the tool. As an alternative to this, the tube can already have been joined to the proximal end of the tool prior to the removal of the substantially helical region.

When the coupling member is provided for the distal end of a shaft, the tube can form the outside tube of the shaft or prior to or after the removal of the substantially helical region, can be joined, in particular welded, soldered or bonded, onto an outside tube of the shaft.

Further possible embodiments, variants, characteristics, features, actions and advantages of a medical instrument correspond to those described above for a tool or a shaft.

In the case of a method, as is described here, a support sleeve is additionally joined onto the coupling member.

The support sleeve can be joined onto the coupling member prior to or after the coupling member has been joined onto the proximal end of the tool. The support sleeve is joined onto the coupling member in particular by means of laser cutting. As the support sleeve and its mechanical connection to the coupling member can be provided and realized such that the support sleeve simply serves for transmitting or diverting forces over a wide area without any local mechanical peak stresses, it can be realized with very thin walls.

Further possible embodiments, variants, characteristics, features, actions and advantages of a method correspond to those described above for a tool or a shaft.

BRIEF DESCRIPTION OF THE DRAWINGS

Embodiments are explained below by way of the accompanying Figures, in which, in detail.

DETAILED DESCRIPTION OF THE INVENTION

Figure 1:
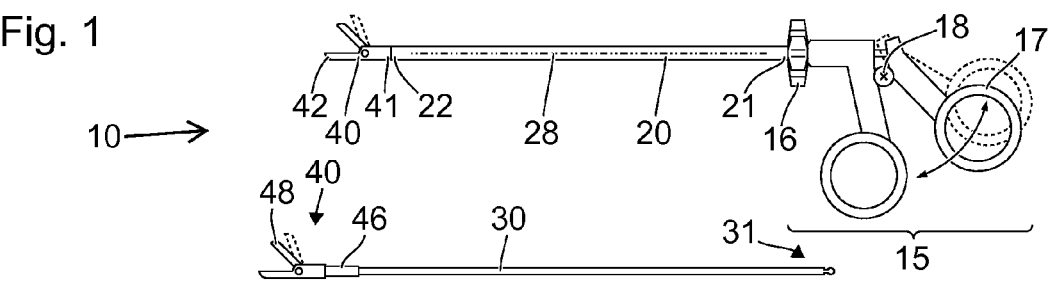
FIG. 1 shows a schematic representation of a medical instrument.

FIG. 1 shows a schematic representation of a medical instrument, in particular a micro-invasive surgical instrument 10 with a handling device 15 on the proximal end, a tool 40 on the distal end and a shaft 20 which connects the handling device 15 to the tool 40. A proximal end 21 of the shaft 20 is coupled in a permanent or releasable manner to the handling device 15. A wheel 16, by means of which the shaft 20 is rotatable about its longitudinal axis 28, is provided on the handling device 15. The handling device 15 also includes a pivotable part 17 which is pivotable about a pivot axis 18 at right angles to the longitudinal axis 28 of the shaft 20.

The distal end 22 of the shaft is releasably connected to the proximal end 41 of the tool 40. At the same time, the distal end 42 of the tool 40 forms the distal end of the medical instrument 10.

Below in FIG. 1, the tool 40 is shown a second time separately from the shaft 20. At its proximal end 41, the tool 40 includes a coupling member 46 for releasable mechanical coupling with the distal end 22 of the shaft 20. In addition, the tool 40 includes a fixed mouth part and a pivotable mouth part 48. As an alternative to this, the tool 40 can include two or more pivotable mouth parts. The tool 40 can be a pair of forceps, a gripper, scissors, a needle holder or another tool having a fixed and a pivotable mouth part or having two or more pivotable mouth parts or having another type of acting device which is movable by means of the transmission rod 30.

The tool is connected to a distal end of a transmission rod 30 for transmitting a force and/or a torque from the handling device 15 to the tool 40. The proximal end 31 of the transmission rod 30 is provided and realized for the purpose of being coupled with the pivotal part 17 of the handling device 15. The distal end of the transmission rod 30 is arranged inside the mouth part 40 and consequently cannot be seen in FIG. 1. The distal end of the transmission rod 30 is coupled directly or indirectly (for example by means of a connecting rod or toggle mechanism) with the pivotable mouth part 48 of the tool 40.

In the fitted together state of the medical instrument 10 shown above in FIG. 1, pivot movements of the pivotable part 17 of the handling device 15 and of the pivotable mouth part 48 of the tool 40 are coupled by means of the transmission rod 30. The continuous lines show the pivotable mouth part 48 of the tool 40 in an open position and the pivotable part 17 of the handling device 15 in a corresponding position. The broken lines show the pivotable mouth part 48 in a super-open position and the pivotable part 17 of the handling device 15 in a corresponding position. The meaning of the super-open position is described in more detail below with reference to FIG. 7.

When the pivotable part 17 is pivoted from the position shown by the continuous line in FIG. 1 further in the distal direction, the pivotable mouth part 48 of the tool 40 is pivoted downward from the position shown by the continuous line, as a result of which gripping, clamping or cutting are possible.

Figure 2:
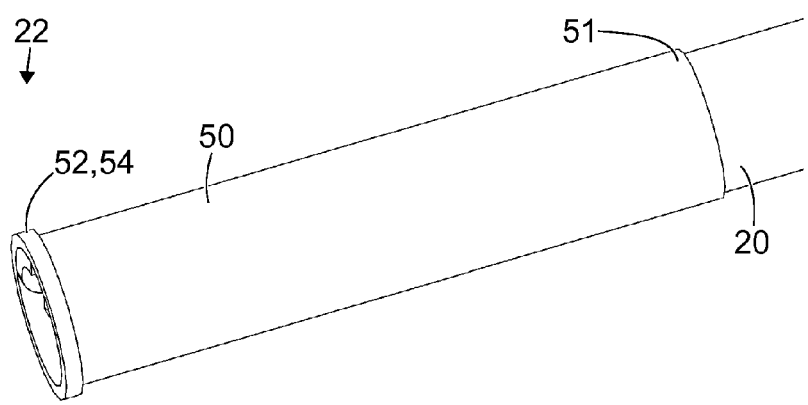
FIG. 2 shows a schematic axonometric representation of part of a distal end of a shaft.

FIG. 2 shows a schematic axonometric representation of the distal end 22 of the shaft 20 without any tool. The shaft 20 is represented in FIG. 2 by a shaft tube which extends from the proximal end 21 as far as up to the distal end 22 (cf. FIG. 1) of the shaft 20. No difference is made between the shaft and the shaft tube below.

On the distal end 22, the shaft tube 20 is surrounded by a thin-walled sleeve 50 having a proximal edge 51 and a distal edge 52. Both the shaft tube 20 and the sleeve 50 essentially have in each case—apart from the exceptions described below—a circular ring-shaped cross section. A radially outwardly protruding collar 54, which stiffens the distal edge 52 of the support sleeve 50, is provided on the distal end 52 of the support sleeve 50.

Figure 3:
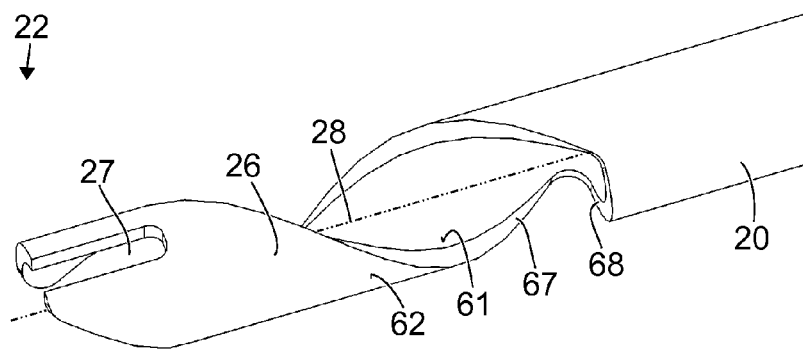
FIG. 3 shows a further schematic axonometric representation of the distal end from FIG. 2.

FIG. 3 shows a further schematic axonometric representation of the distal end 22 of the shaft 20. The schematic axonometric representation in FIG. 3 corresponds to FIG. 2 with regard to the viewing direction and the detail shown. The representation in FIG. 3 differs from the representation in FIG. 2 in that the support sleeve 50 has been removed.

On its distal end 22, the shaft tube 20 is not in the form of a complete circular cylinder. Rather, the shaft tube 20 has been re-formed close to its distal end 22 to form a substantially helical-strip-shaped coupling member 26. The coupling member 26 has an inner lateral surface 61 and an outer lateral surface 62. The inner and the outer lateral surfaces 61, 62 are in each case cutouts from circular cylinder barrels (therefore as faces in mathematical terms). The edge of the coupling member 26 includes two helical portions 67 (only one of which is provided with the reference in FIG. 3) and one circumferential portion 68.

The coupling member 26 has a notch 27, the function of which is described below in more detail with reference to FIG. 7. The notch 27 extends from the distal edge of the shaft tube 20 or of the coupling member 26 in the direction parallel to the longitudinal axis 28 of the shaft tube 20.

Figure 4:
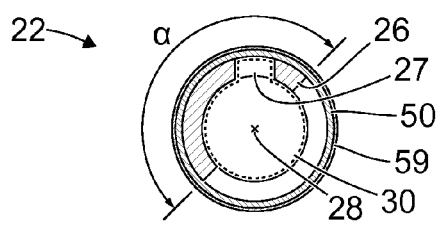
FIG. 4 shows a schematic representation of a section through the distal end from FIGS. 2 and 3.

FIG. 4 shows a schematic representation of a section through the distal end 22 of the shaft 20 along a plane at right angles to the longitudinal axis 28. The sectional plane lies close to the distal edge directly proximally of the collar 54 of the support sleeve 50.

The coupling member 26 extends in the circumferential direction over an angle α (alpha) of approximately 180°. The coupling member 26 is surrounded by the thin-walled support sleeve 50, the circular cross section of which can be seen in FIG. 4. The support sleeve 50 and the shaft tube 20 (cf. FIGS. 2 and 3) are surrounded by a shrink-on tube 59. The shrink-on tube 59, which is not shown in FIG. 2, connects directly proximally to the collar 54 on the distal edge 52 of the support sleeve 50. Another casing, which can enable, in particular, electric insulation of the shaft 20 in relation to the surrounding area, can be provided in place of the shrink-on tube 59.

The contour of a transmission rod, which can be inserted into the shaft, is shown by the broken line in the lumen of the shaft tube 20 or of the coupling member 26.

Figure 5:
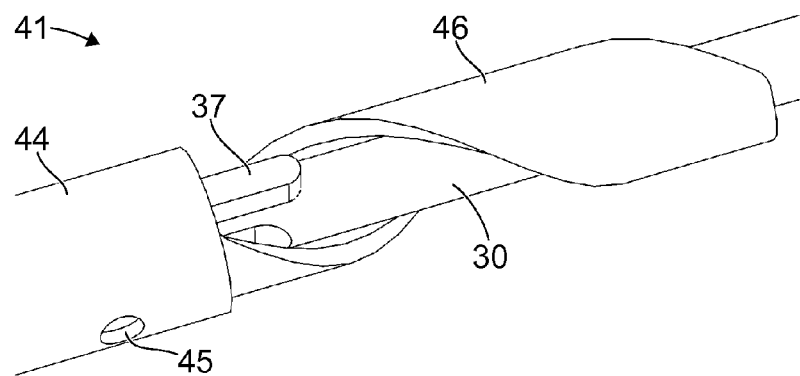
FIG. 5 shows a schematic axonometric representation of a proximal end of a tool.

FIG. 5 shows a schematic axonometric representation of the proximal end 41 of a tool 40, as is shown above by way of FIG. 1. The schematic axonometric representation of FIG. 5 corresponds to the representations of FIGS. 2 and 3 with regard to the viewing direction.

The tool 40 has a coupling member 46 in the form of a helical-strip-shaped cutout of a circular cylinder barrel. In addition, a transmission rod 30, as is shown above by way of FIG. 1, is arranged so as to be displaceable parallel to its longitudinal axis 28 inside the coupling member 26. In the case of the example shown in FIG. 5, the transmission rod 30 has a circular cross section, the diameter of which, in terms of a clear representation and a clear ability to distinguish from the coupling member 46, is smaller than the cross section surrounded by the coupling member 46. Deviating from the representation in FIG. 5, the transmission rod 30 can abut on the inside against the coupling member 46 or abut in a substantial manner or have an outer cross section which is only slightly smaller than the inner cross section of the coupling member 46.

A component 44 of the mouth part 40, which is tubular in the detail shown, can also be seen in FIG. 4. The distal end of the component 44, which is not shown in FIG. 4, includes, in particular, a fixed mouth part and/or one or several pivotable mouth parts 48 (cf. FIG. 1). The function of an opening 45 on the component 44 is described below with reference to FIG. 6. A locking bar 37, the function of which is described in more detail below with reference to FIG. 7, is realized on the transmission rod 30.

Figure 6:
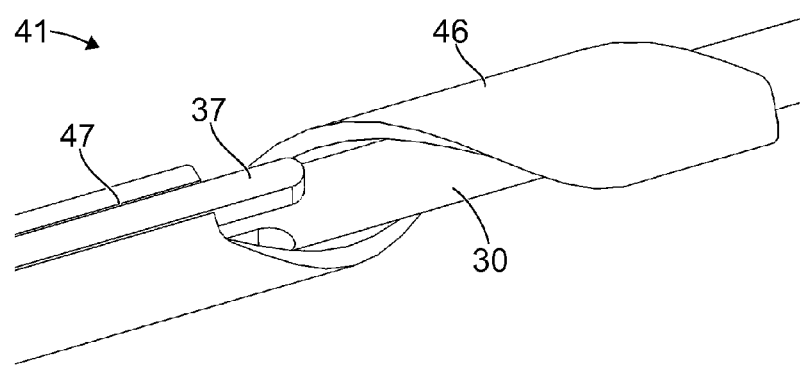
FIG. 6 shows a further schematic axonometric representation of the proximal end from FIG. 5.

FIG. 6 shows a further schematic axonometric representation of the proximal end 41 of the tool 40 from FIG. 5. The schematic axonometric representation in FIG. 6 corresponds to the representation in FIG. 5 with regard to the viewing direction and the detail shown.

The representation in FIG. 6 differs from the representation in FIG. 5 in that the component 44 of the tool 40 is not shown. The distal end of the coupling member 46 is substantially tubular with a longitudinal slot or a notch 47 for the locking bar 37. The opening 45 which can be seen in FIG. 5 in the sleeve-shaped component part of the tool 40 or several of these types of openings serve for a positively bonded connection between the component 44 and the coupling member 46 by means of laser welding or in another manner.

Figure 7:
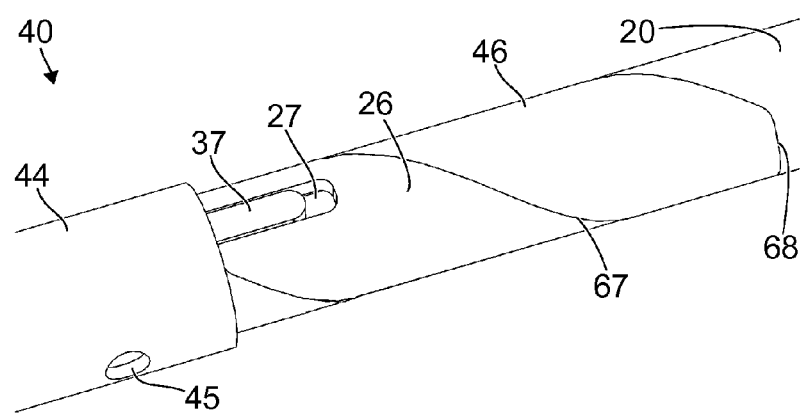
FIG. 7 shows a schematic axonometric representation of a proximal end of a tool and a distal end of a shaft which are coupled together.

FIG. 7 shows a schematic axonometric representation of a releasable, positive locking, mechanical connection between the tool 40, shown above by way of FIGS. 1, 5 and 6, and the distal end of the shaft 20 shown above by way of FIGS. 1 to 4. The schematic axonometric representation in FIG. 7 corresponds to the representations of FIGS. 5 and 6 with regard to the viewing direction and the detail shown.

The helical-strip-shaped coupling member 26 on the shaft 20 and the helical-strip-shaped coupling member 46 on the tool 40 interlock and form a positive locking, mechanical connection between the shaft 20 and the tool 40. In this case, the coupling members 26, 46 complement one another essentially to form a complete circular cylinder barrel. The helical portions 67 and the circumferential portions 68 of the edges of the coupling members 26, 46 essentially abut against one another or are only separated in each case by a small gap.

The locking bar 37 on the transmission rod 30 (cf. FIGS. 5 and 6) engages in the notch 27 on the coupling member 26. As the locking bar—as indicated as an example in FIG. 6—is only axially displaceable in the tool 40, the positive locking connection between the coupling members 26, 46 is locked by the engagement of the locking bar 37 in the notch 27. The tool 40 and in particular the locking bar 37 are realized such that the locking bar 37 no longer engages in the notch 27 when the pivotable mouth part 48 of the tool 40 assumes the super-open position shown in FIG. 1 by the broken line. Consequently, in the super-open position of the pivotable mouth part 48, the tool 40 is able to be coupled with the distal end 22 of the shaft 20 and released again from said distal end of the shaft.

Figure 8:
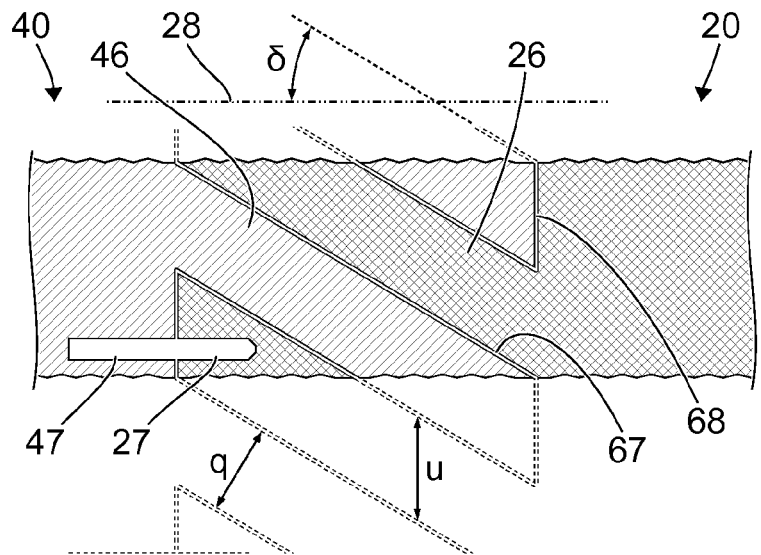
FIG. 8 shows a schematic representation of a developed view of coupling members.

FIG. 8 shows a schematic representation of a developed view of the coupling members 26, 46 on the shaft 20 and on the tool 40 which are shown above with reference to FIGS. 1 to 7. The developed view corresponds to a transformation of or an imaging of a circular cylinder barrel into a plane. The intersection line, along which the circular cylinder is cut open, is shown in a wavy manner and is arranged horizontally just as the axis of symmetry of the circular cylinder.

The coupling members 26, 46 are shown with different hatching so as to distinguish better between them. The edges of the coupling members 26, 46 are shown, for reasons of simplicity, as being composed of helical portions 67 and circumferential portions 68, each of which is straight in the developed view. The rounded transitions, which can be seen in FIGS. 3 and 5 to 7, between the helical portions 67 and the circumferential portions 68, which can reduce the notch effect and increase the robustness, are not shown in FIG. 8 for reasons of simplicity.

The helical portions 67 of the edges of the coupling members 26, 46 enclose an angle δ (delta) with the longitudinal axis 28 (cf. FIGS. 1, 3). The width u of each helical-strip-shaped coupling portion 26, 46, measured in the circumferential direction, is half the overall circumference $U=\pi \times d$ (U=pi times d) of the shaft tube 20, wherein d is the diameter of the shaft tube 20. The angle α (alpha) shown in FIG. 4 is (in radian) α=u/U (alpha=u divided by U). The width q of the coupling members 26, 46, measured at right angles to the helical portions 67 of the edges of the coupling members 26, 46, is $q=u \times \sin(\delta)$ (q=u times sin(delta)).

The greater the angle δ (delta) between the helical edges 67 of the coupling members 26, 46 and the longitudinal axis 28, the smaller the width q measured in the direction at right angles to the helical edges 67. However, at the same time as δ (delta) increases, the length of the helical-strip-shaped coupling members 26, 46, measured parallel to the helical edges 67, also decreases. An angle δ (delta) which is advantageous with regard to the mechanical rigidity of the helical-strip-shaped coupling members 26, 46 is approximately 60°.

Figure 9:
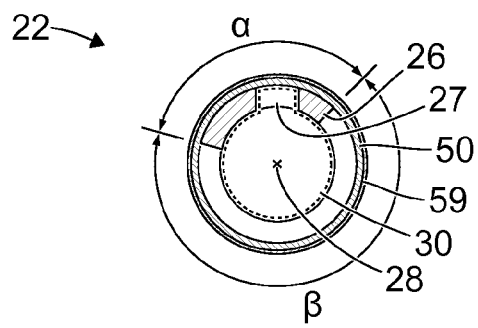
FIG. 9 shows a schematic representation of a cross section of a variant of a coupling member.

FIG. 9 shows a schematic representation of a section along a cutting plane at right angles to the longitudinal axis 28 through a distal end of a shaft, which is similar in some features to the exemplary embodiment shown above by way of FIGS. 1 to 4, 7 and 8. The representation in FIG. 9 corresponds to the representation in FIG. 4 with regard to the position of the cutting plane shown directly proximally of a collar 54 on the distal end 52 of a support sleeve 50.

The exemplary embodiment shown in FIG. 9 differs from the exemplary embodiment shown above by way of FIGS. 1 to 8 in that the two corresponding coupling members 26, 46 are different in width. The coupling member 26 on the distal end of the shaft has in the circumferential direction a width α (alpha) which is approximately 120°. The coupling member not shown in FIG. 9 on the distal end of the shaft extends in the circumferential direction over an angle β (beta) of approximately 240°. As the rigidity of the coupling member 26 on the distal end of the shaft 20 is increased by the support sleeve 50, approximately identical mechanical rigidities can be achieved when the coupling members have different widths.

Figure 10:
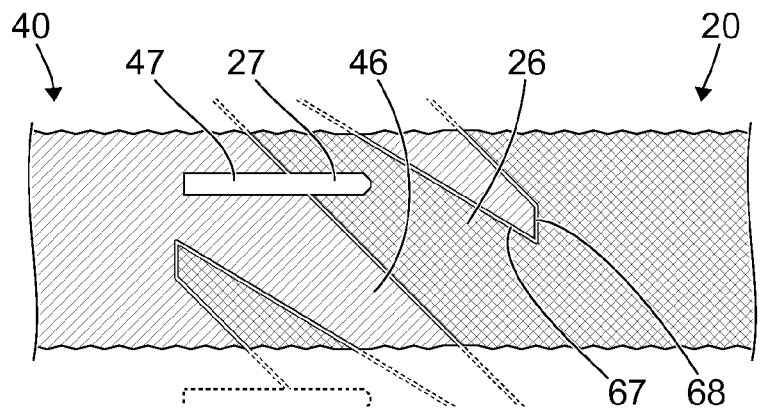
FIG. 10 shows a schematic representation of a developed view of coupling members.
Figure 11:
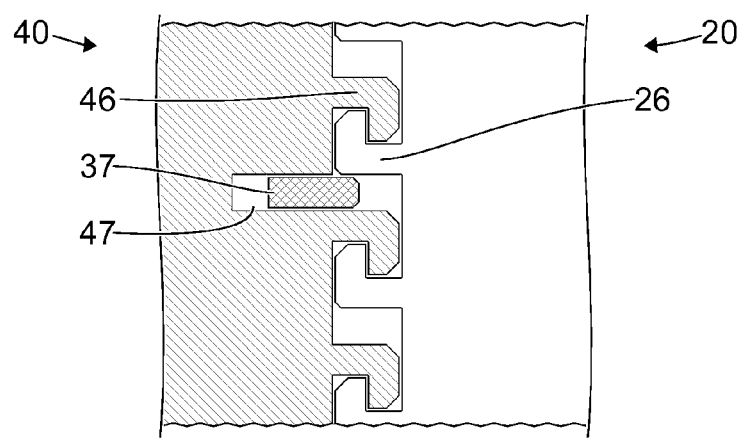
FIG. 11 shows a schematic representation of a developed view of coupling members'.

FIGS. 10 and 11 show schematic representations of two further exemplary embodiments of a mechanical coupling between a tool 40 and a shaft 20. Corresponding to the representation in FIG. 8, the representations in FIGS. 10 and 11 shows a developed view of the coupling members 26, 46 on the shaft 20 and on the tool 40 into the drawing plane. The exemplary embodiments of FIGS. 10 and 11 are in each case similar to the exemplary embodiment in FIGS. 1 to 8 in some features which are not described again below.

In the case of the exemplary embodiment shown in FIG. 10, the coupling members 26, 46 on the shaft 20 and the tool 40 are in each case in the form of a substantially helical-wedge-shaped cutout from a circular cylinder barrel. The two helical portions 67 of the edges of a coupling member 26, 46 have different pitches or enclose different angles with the longitudinal axis 28 (cf. FIGS. 1, 3, 8). Consequently, the width of the coupling member 26 in the shaft 20, measured in the direction of the circumference of the circular cylinder barrel or at right angles to the longitudinal axis 28, decreases in the distal direction (on the left in FIG. 10) and the width of the coupling member 46 on the tool 40 decreases in the proximal direction (on the right in FIG. 10).

Deviating from the helical-wedge-shaped form, a notch 27 is provided on the coupling member 26 on the shaft 20 and a notch 47 is provided on the coupling member 46 on the tool 40. Similarly as in the case of the exemplary embodiment shown by way of FIGS. 1 to 7, a locking bar, which is not shown in FIG. 10, is displaceable axially or parallel to the longitudinal axis 28 in the notch 47. When the locking bar engages in the notch 47 in the tool 40 and in the notch 27 in the shaft 20 at the same time, it locks the mechanical coupling between the tool 40 and the shaft 20.

In the case of the exemplary embodiment shown in FIG. 11, the coupling members 26, 46 on the shaft 20 and the tool 40 have in each case a substantially hook-shaped or L-shaped form. Both the shaft 20 and the tool 40 have, in each case, hook-shaped coupling members 26, 46 which are evenly distributed over the circumference. The number of hook-shaped coupling members 26 on the shaft corresponds to the number of coupling members 46 on the tool. In the case of the example shown, the shaft 20 and the tool 40 each have three coupling members 26, 46.

Each coupling element 26 on the shaft 20 has an axial portion which extends parallel to the longitudinal axis 28 (cf. FIGS. 1, 3, 8), and on its distal end has a circumferential portion which extends at right angles to the longitudinal axis 28. Each coupling member 46 on the tool 40 has an axial portion which extends parallel to the longitudinal axis 28, and on its proximal end has a circumferential portion which extends at right angles to the longitudinal axis 28.

The coupling elements are realized in particular with regard to their dimensions and their spacings such that the mechanically coupled situation shown in FIG. 11 can be produced by a relative axial and subsequent rotational movement of the tool 40 and the shaft 20. In this case, the circumferential portions of the coupling members 46 on the tool 40 lie in part proximally of the circumferential portions of the coupling members 26 on the shaft 20. The locking bar 37 can lock the mechanical coupling between the tool 40 and the shaft 20. The mechanically coupled situation shown in FIG. 11 can be released again by a reversed relative rotational and a subsequent axial movement.

In the case of the exemplary embodiments shown above by way of FIGS. 1 to 11, the coupling member 26, 46 is arranged on a proximal end 41 of a tool 40 or on a distal end 22 of a shaft 20. Where the coupling member 26, 46 is used in this manner, it can be advantageous for the coupling member 26, 46 to be able to be miniaturized to a certain extent. This can make particularly small cross sections of the shaft and of the tool possible. However, as an alternative to this, similar coupling members can be used on the proximal end 21 of a shaft 20 (for releasable mechanical coupling with a distal end of a further shaft or shaft portion or with a distal end of a handling device) or on the distal end of a handling device 15 (for releasable mechanical coupling with a proximal end 21 of a shaft 20).

Figure 12:
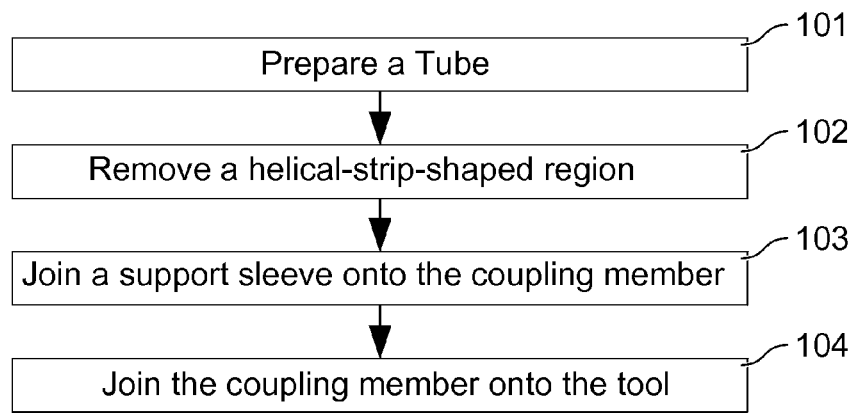
FIG. 12 shows a schematic flow diagram.

FIG. 12 shows a schematic flow diagram of a method for producing a coupling member for or on a proximal end of a tool or for or on a distal end of a shaft or for or on a proximal end of a shaft or for or on a distal end of a handling device for a medical instrument. Although the method can also be used to produce coupling members which differ from those shown above by way of FIGS. 1 to 9, references from FIGS. 1 to 9 are used below as an example in order to improve comprehensibility.

A tube with a circular ring-shaped cross section is prepared in a first step 101. When a coupling member is to be produced on a proximal end 21 or on a distal end 22 of a shaft 20, the tube can be the shaft tube which forms the shaft 20 or the essential component part thereof.

A region of the tube is removed in order to form the coupling member 26, 46 in a second step 102. In particular, a helical-wedge-shaped or helical-strip-shaped region is removed, the coupling member 26, 46 also having a helical-wedge-shaped or a helical-strip-shaped form. As an option, a notch 27 can also be generated on the coupling member for a locking process produced by means of a locking bar 37 which engages in the notch 27.

In an optional third step 103, a support sleeve 50 is joined, in particular welded, soldered or bonded, onto the coupling member 26, 46.

If the tube on which the coupling member 26, 46 has been formed in the second step 102, is not the shaft tube of a shaft 20, in a fourth step 104 the coupling member 26, 46 (where applicable together with the support sleeve 50) can be joined onto the proximal end of the tool or onto the proximal end 21 or onto the distal end of the shaft 20. As an alternative to this, the fourth step 104 can already have been carried out prior to the second step 102.

REFERENCES

10 Medical instrument
15 Handling device on the proximal end of the medical instrument 10
16 Wheel on the handling device 15
17 Pivotable part of the handling device 15
18 Pivot axis of the pivotable part 17
20 Shaft of the medical instrument 10
21 Proximal end of the shaft 20
22 Distal end of the shaft 20
26 Coupling member on the distal end 41 of the shaft 20
27 Notch on the coupling member 26
28 Longitudinal axis of the shaft 20
30 Transmission rod
31 Proximal end of the transmission rod 30
37 Locking bar on the distal end of the transmission rod 30
40 Tool
41 Proximal end of the tool 40
42 Distal end of the tool 40
44 Component of the tool 40
45 Opening for welding connection
46 Coupling member on the proximal end 41 of the tool 40
47 Notch on the coupling member 46
48 Pivotable mouth part of the tool 40
50 Support sleeve on the coupling member 26
51 Proximal edge of the support sleeve 50
52 Distal edge of the support sleeve 50
54 Collar on the distal edge 52 of the support sleeve 50
59 Shrink-on tube
61 Inner lateral surface
62 Outer lateral surface
67 Helical portion of the edge of the coupling member 26
68 Circumferential portion of the edge of the coupling member 26
101 First step (Prepare a tube)
102 Second step (Remove a helical-strip-shaped region of the tube)
103 Third step (Join a support sleeve onto the coupling member)
104 Fourth step (Join the coupling member onto the proximal end of a tool)
α (Alpha) angle over which the coupling member 26 extends in the circumferential direction
β (Beta) angle over which the coupling member 46 extends in the circumferential direction
δ (Delta) angle between the helical portion 67 and the longitudinal axis 28
q Width of the coupling member 26 measured at right angles to the helical portion 67
u Width of the coupling member 26 measured in the circumferential direction

The invention claimed is:
1. A medical instrument, comprising:
a shaft;
a tool;
a first coupling member on a distal end of the shaft; and
a second coupling member on a proximal end of the tool, the second coupling member configured to be releasably mechanically coupled with the first coupling member;
wherein the first coupling member is in a form of a substantially helical cutout from a first circular cylinder barrel and the second coupling member is in a form of a substantially helical cutout from a second circular cylinder barrel, wherein the first circular cylinder barrel and the second circular cylinder barrel have the same diameter;

wherein the first coupling member includes a notch extending into a distal end of the first coupling member in a direction parallel to a longitudinal axis of the shaft.

2. The medical instrument according to claim 1, where the first coupling member is in the form of a helical-strip-shaped cutout of said first circular cylinder barrel or in the form of a cutout of said first circular cylinder barrel, a width of which reduces continuously or discontinuously in a proximal direction.

3. The medical instrument according to claim 1, said tool additionally comprising:
a transmission rod configured to transmit at least one of a force or a torque between a proximal end of said shaft and said distal end of said shaft which is coupled with the tool,
wherein an inside diameter of the first circular cylinder barrel corresponds substantially to an outside diameter of the transmission rod.

4. The medical instrument according to claim 1, said tool additionally comprising:
a support sleeve which abuts against the first coupling member and is joined to the first coupling member.

5. The medical instrument according to claim 2, where a width of the helical-strip-shaped cutout of the first circular cylinder barrel in a circumferential direction corresponds to half of a circumference of the first circular cylinder barrel.

6. The medical instrument according to claim 1, where the second coupling member is in the form of a helical-strip-shaped cutout of said second circular cylinder barrel or in the form of a cutout of said second circular cylinder barrel, a width of which reduces continuously or discontinuously in a proximal direction.

7. The medical instrument according to claim 6, where a width of the helical-strip-shaped cutout of the second circular cylinder barrel in a circumferential direction corresponds to half of a circumference of the second circular cylinder barrel.

8. The medical instrument according to claim 1, wherein the tool includes a transmission rod configured to transmit at least one of a force or a torque between a proximal end of said shaft and said distal end of said shaft which is coupled with the tool; and
wherein a distal end of the transmission rod includes a locking bar configured to engage the notch of the first coupling member to thereby prevent the first coupling member from rotating relative to the second coupling member.

9. A medical instrument, comprising:
a tool having a coupling member on a proximal end of the tool, the coupling member configured to be releasably mechanically coupled with a distal end of a shaft of said medical instrument, said coupling member is in a form of a substantially helical cutout of a first circular cylinder barrel; and
a handling device which can be taken apart in a non-destructive manner, said handling device having a coupling;
said coupling of said handling device having a corresponding coupling member, the corresponding coupling member configured to be releasably mechanically coupled with said coupling member of said tool, wherein the corresponding coupling member is in a form of a substantially helical cutout of a second circular cylinder barrel;
wherein the coupling member of the handling device includes a notch extending into a distal end of the coupling member in a direction parallel to a longitudinal axis of the handling device.

10. The medical instrument according to claim 9, where the coupling member of the handling device is in the form of a helical-strip-shaped cutout of said second circular cylinder barrel or in the form of a cutout of said second circular cylinder barrel, a width of which reduces continuously or discontinuously in a proximal direction.

11. The medical instrument according to claim 9, where said tool additionally comprises:
a transmission rod configured to transmit at least one of a force or a torque between a proximal end of said shaft and said distal end of said shaft which is coupled with the tool,
wherein an inside diameter of the second circular cylinder barrel corresponds substantially to an outside diameter of the transmission rod.

12. The medical instrument according to claim 9, where said tool additional comprises:
a support sleeve which abuts against the coupling member of the handling device and is joined to the coupling member of the handling device.

13. The medical instrument according to claim 10, where a width of the helical-strip-shaped cutout of the second circular cylinder barrel in a circumferential direction corresponds to half of a circumference of the second circular cylinder barrel.

14. The medical instrument according to claim 9, wherein the tool includes a transmission rod configured to transmit at least one of a force or a torque between said handling device and said tool; and
wherein a distal end of the transmission rod includes a locking bar configured to engage the notch of the coupling member of the handling device to thereby prevent the coupling member of the handling device from rotating relative to the coupling member of the tool.

* * * * *